United States Patent [19]

Drent et al.

[11] Patent Number: 5,350,876
[45] Date of Patent: Sep. 27, 1994

[54] CARBONYLATION OF CONJUGATED DIENES

[75] Inventors: Eit Drent; Willem W. Jager, both of Amsterdam, Netherlands

[73] Assignee: Shell Oil Company, Houston, Tex.

[21] Appl. No.: 82,213

[22] Filed: Jun. 24, 1993

[30] Foreign Application Priority Data

Jun. 29, 1992 [EP] European Pat. Off. ........... 92201941

[51] Int. Cl.⁵ ............................................. C07C 67/36
[52] U.S. Cl. ..................................................... 560/207
[58] Field of Search .......................................... 560/207

[56] References Cited

U.S. PATENT DOCUMENTS

| | | | |
|---|---|---|---|
| 4,172,087 | 10/1979 | Knifton | 260/410.6 |
| 4,739,110 | 4/1988 | Drent | 560/207 |
| 4,824,817 | 4/1989 | Drent | 560/207 |
| 4,894,474 | 1/1990 | Maerial et al. | 560/207 |
| 4,925,973 | 5/1990 | Deweerdt et al. | 560/204 |
| 5,026,901 | 6/1991 | D'Amore | 560/207 |
| 5,028,734 | 7/1991 | Drent | 560/207 |

FOREIGN PATENT DOCUMENTS

| | | |
|---|---|---|
| 0273489 | 7/1088 | European Pat. Off. . |
| 190473 | 8/1986 | European Pat. Off. . |
| 0271145 | 6/1988 | European Pat. Off. . |
| 0284170 | 9/1988 | European Pat. Off. . |
| 0441446 | 8/1991 | European Pat. Off. . |
| 2498594 | 7/1982 | France . |
| 50-000645 | 1/1975 | Japan . |
| 1110405 | 4/1968 | United Kingdom . |
| 1600525 | 10/1981 | United Kingdom . |

*Primary Examiner*—Paul J. Killos

[57] ABSTRACT

The invention relates to a process for the preparation of alkenoic acid derivatives by reaction of an aliphatic conjugated diene with carbon monoxide and a hydroxyl group-containing compound. The reaction is carried out in a liquid reaction medium of controlled polarity in the presence of a catalyst system containing a palladium compound, a multidentate phosphine ligand, and optionally a protonic acid. By controlling the polarity of the reaction medium to a calculated dielectric constant $\epsilon_{calc}$ of below a value of 8, higher reaction rates are achieved.

10 Claims, No Drawings

CARBONYLATION OF CONJUGATED DIENES

FIELD OF THE INVENTION

This invention relates to a process for the preparation of alkenoic acid derivatives by reaction of aliphatic conjugated dienes with carbon monoxide and hydroxyl group-containing compounds.

BACKGROUND OF THE INVENTION

Alkenoic acid derivative products obtainable by the present process, such as alkenoic esters, acids and anhydrides, constitute versatile intermediates for various chemical products. They become particularly accessible if cheap base feedstock, such as butadiene can be used. Alkyl 3-pentenoates, for example, are intermediates to dialkyl adipates and 6-oxohexanoates in an efficient manufacturing route to polyamide-6,6 and polyamide-6, respectively.

U.S. Pat. No. 4,172,087 discloses a process for the carbonylation of conjugated dienes in the presence of an alcohol and using a catalyst system containing a halide-free palladium salt, a multidentate phosphine ligand and tertiary nitrogen base (e.g., pyridine, quinoline or isoquinoline). The tertiary nitrogen base is used in large excess relative to the other catalyst system components, and essentially serves as the solvent for the reaction. In the absence of added N-heterocyclic solvent, considerable precipitation of palladium-containing insoluble species occurs and much lower product yields are reported. This known process involves two concurrent reactions, viz. dimerization and carbonylation, and mixed reaction products (e.g., isopropyl pentenoate and isopropyl nonadienoate) were obtained.

Subsequent improvement in terms of selectivity of the conjugated diene carbonylation was disclosed by EP-A-273489. In EP-273489, the reaction is carried out in the presence of a specific substantially organic nitrogen-containing base-free catalyst system containing a palladium compound in conjunction with at least one multidentate organic phosphorus ligand. Specifically in a preferred embodiment, a catalytic quantity of a protonic acid with a pKa value > 3 is added to increase the yield of, for example, pentenoates in the case of conversion of butadiene emphasizing the desirability of avoiding the basic reaction medium used according to U.S. Pat. No. 4,172,087. The process of EP-A-273489 affords the carbonylation of butadiene to proceed with a selectivity to alkyl pentenoates of about 90% or higher.

The known processes provide an interesting route to alkenoic acid derivatives from cheap feedstock, but their reaction rates in relation to the amount of precious palladium catalyst component applied leaves room for further improvement for providing an industrially viable process. In particular, for the production of polyamides further improvement is necessary to compete with commercial technology.

It is therefore an object of the present invention to provide an improved process to produce alkenoic acid derivatives from aliphatic conjugated dienes.

SUMMARY OF THE INVENTION

According to the invention, a process for the preparation of alkenoic acid derivatives is provided, comprising reacting an aliphatic conjugated diene with carbon monoxide and a hydroxyl group-containing compound in a reaction medium of controlled polarity in the presence of a catalyst system comprising a palladium compound, a multidentate phosphine ligand, and optionally a protonic acid.

DETAILED DESCRIPTION OF THE INVENTION

It has been found that by carefully controlling the polarity of the medium during the course of the carbonylation reaction, higher reaction rates are achieved than the above-mentioned processes while maintaining excellent selectivities even when an organic nitrogen-containing base is present. According to the invention, high polarities of the reaction medium are to be avoided for it retards the reaction. Too low a polarity of the reaction medium may also not be suitable due to reduced solubility of the catalyst metal component.

The process of the invention can be carried out while the polarity of the liquid reaction medium is continuously monitored. The present process also provides for a convenient criteria for assessing the required polarity of the reaction medium. According to a preferred embodiment of the present process, the calculated dielectric constant $\epsilon_{calc}$ of the reaction medium is below a value of 8, preferably at a value within the range of from about 4.5 to about 7.5, most preferably within the range of from about 5 to about 6.5 during the course of the reaction. To this end, $\epsilon_{calc}$ is calculated as the volume average of the dielectric constants at 25° C. of the pure liquid substrates and solvents present in the reaction medium, which data are available from literature. Though in this approach minor influences from dissolved amounts of carbon monoxide and catalyst components are neglected, for practical purposes the criteria has appeared to be sufficiently accurate for distinguishing the polarity condition required for improved reaction rates of the carbonylation reaction. The prior processes were all conducted in a reaction medium of $\epsilon_{calc}$ of above 8.

The liquids to be taken into account for calculating $\epsilon_{calc}$ usually will be the aliphatic conjugated diene, the hydroxyl group-containing compound and the solvent or solvents, if any. It is conceivable, that alkenoic acid derivative product formed during the course of the reaction, may contribute to the average dielectric constant of the liquid reaction mixture. However, the dielectric constants of these products generally fall within the range of from about 5 to about 6.5, which is preferred for the liquid reaction mixture and therefore will have a minor or negligible contribution to the average dielectric constant, when the process is carried out in accordance with the invention.

In the present context, the dielectric constant for a given liquid is used in its normal meaning of representing the ratio of the capacity of a condenser with that substance as dielectric to the capacity of the same condenser with a vacuum for dielectric. Values for the dielectric constants of common organic liquids may be found in general reference books, such as the Handbook of Chemistry and Physics, Edited by CRC, or more specialized publications, and are usually quoted for a temperature of 25° C., or can be readily converted to that temperature using the conversion factors quoted. If no literature data for a particular compound are available, the dielectric constant may be readily measured by using established physico-chemical methods. Dielectric constant $\epsilon_{calc}$ is calculated as the volume average of the dielectric constants at 25° C. of the pure liquid substrates and solvents.

For example, for ethanol $\epsilon=24.3$, for diphenyl ether $\epsilon=3.7$ and for 1,3-butadiene $\epsilon=1.9$ (For butadiene, by extrapolation of the data in J. Chem. Thermodynamics, 1986, 18, 221-234). On this basis, a volume averaged dielectric constant $\epsilon_{calc}$ of 8.4 is calculated for a mixture of 15 ml ethanol, 40 ml diphenyl ether and 8 ml butadiene ($15/63 \times 24.3 + 40/63 \times 3.7 + 8/63 \times 1.9 = 8.4$) as used in Example 1 of EP-A-273489. Similarly, a reaction medium of 40 ml pyridine ($\epsilon=12.3$), 20 ml isopropanol ($\epsilon=18.3$), and 32 ml 1,3-butadiene, as used in Example 12 of U.S. Pat. No. 4,172,087, has an $\epsilon_{calc}$ of 10.0. If containing quinoline or isoquinoline, as in Examples 1 or 3 of U.S. Pat. No. 4,172,087, the reaction medium has an $\epsilon_{calc}$ of 8.6 or 9.3, respectively.

Substrates, solvents and catalyst components of the present process can be the same as those used in the prior processes. However, by judicious combination and/or selection of the concentrations of the reaction medium according to the present invention, the polarity of the reaction medium can be controlled such that the desired increase of reaction rate is achieved.

Preferable aliphatic conjugated dienes include alkadienes, preferably having from 4 to 8 carbon atoms, such as 1,3-butadiene ($\epsilon=1.9$), 1,3-pentadiene ($\epsilon=2.32$), 1,3-hexadiene, cis,cis-2,4-hexadiene ($\epsilon=2.16$), trans,trans-2,4-hexadiene ($\epsilon=2.12$), 1,3-cyclohexadiene, 2,4-heptadiene and the like, which may carry substituents not interfering with carbonylation reaction, for example alkyl substituents, such as in 2-methyl-1,3-butadiene ($\epsilon=2.10$).

Representative hydroxyl group-containing compounds include alcohols, carboxylic acids and water, of which the alcohols yielding alkenoic esters in the carbonylation reaction are preferred. The alcohols may be aliphatic or aromatic, such as phenol. The use of water yields alkenoic acids, and the use of carboxylic acids alkenoic anhydrides. Typical examples include methanol ($\epsilon=32.6$), ethanol ($\epsilon=24.3$), isopropanol ($\epsilon=18.3$), n-butanol ($\epsilon=17.1$), sec-butanol ($\epsilon=15.8$), isobutyl alcohol ($\epsilon=17.7$) and tert.-butanol ($\epsilon=11.5$). The alcohol may be polyfunctional, such as ethylene glycol ($\epsilon=37.7$), 1,3-propanediol ($\epsilon=35.0$) or glycerol ($\epsilon=42.5$).

The preferred substrates for the present process are 1,3-butadiene in conjunction with an alkanol having from 1 to 4 carbon atoms, which by the reaction with carbon monoxide yield alkyl esters of pentenoic acid, in particular of the 3-pentenoic acid isomer.

The alcohol reactants significantly contribute to the average dielectric constant, in particular methanol and ethanol. Therefore, for controlling the polarity of the reaction medium according to the first embodiment of the invention, the hydroxyl group-containing compound in the carbonylation process is an alkanol having an dielectric constant $\epsilon$ at 25° C. of below 20. More preferably the alkanol is isopropanol or tert-butanol.

According to an alternative embodiment of the invention, the polarity of the reaction medium can also be controlled by assuring that its concentration does not exceed 20% vol of the liquid reaction medium during the course of the reaction, particularly when the hydroxyl group-containing compound is an alkanol having an dielectric constant at 25° C. of above 20. This may be achieved by dilution of the reaction mixture with relatively large amounts of a low polar solvent with concurrent reduction of the concentration of the other substrates. This may render the process unduly cumbersome in view of excessively large liquid streams including any recycling. More preferably, the polarity is controlled by starting the reaction at low concentration of the alkanol, which may be substoichiometric, and the converted amounts of alkanol being repleted by continuous or intermittent further addition of alkanol during the course of the reaction. Accordingly, the cheaper alcohols such as ethanol can also be used in the present process so that methyl and ethyl esters may be prepared, if so desired.

If it is desired to use an alkanol having an dielectric constant at 25° C. of above 30, such as methanol, most preferably it is continuously or intermittently added during the course of the reaction, such that its concentration does not exceed 12% vol of the liquid reaction medium.

The reaction is conducted in the reaction medium in the presence of a catalyst system containing a palladium compound, a multidentate phosphine ligand, and optionally a protonic acid.

The catalyst system useful in the present process contains a palladium compound which may be derived from any source of palladium, which will dissolve in the reaction medium to a sufficient extent for forming the catalytically active species with the other catalyst components. Suitable sources of palladium include salts, such as palladium acetate, palladium acetylacetonate, palladium sulphate and palladium nitrate, and coordination complexes, such as tetrakis triphenylphosphine palladium. Preferably the source of palladium is free of halide. Palladium may be used in a heterogeneous form, for example loaded on an ion exchange resin containing sulfonic acid groups.

The multidentate phosphine ligand contains at least two phosphine P atoms being interconnected by a bridging group allowing for bidentate coordination of the ligand to the palladium metal atom. Preferable ligands are those of formula $R_1R_2>P\text{---}R\text{---}P<R_3R_4$, wherein $R_1$, $R_2$, $R_3$ and $R_4$ represent hydrocarbyl groups, for example aryl or (cyclo)alkyl groups, optionally substituted with one or more substituents and R represents a divalent organic bridging group with at least two carbon atoms forming the bridge. Preferably R represents an alkylene group having three or four carbon atoms, most preferably four carbon atoms. Examples of particularly suitable multidentate phosphine ligands are: 1,3-di(diphenylphosphino)propane, 1,4-di(diphenylphosphino)butane and 1,4-di(di-n-butylphosphino)butane. The molar ratio of multidentate phosphine ligand to palladium gram atoms generally is within the range of from about 1 to about 10. Other phosphines, in particular monophosphines, may additionally be present in the catalyst system.

The catalyst system may further, as an optional component, contain a weak protonic acid, for example having a $pKa>3$. The protonic acid preferably is a sterically hindered carboxylic acid, such as 2,4,6-trimethylbenzoic acid, 2,6-dichlorobenzoic acid or 9-anthroic acid. In general, the amount of protonic acid used is within the range of from about 2 to about 50 equivalents of acid per gram atom of palladium. The protonic acid may be neutralized in part or entirely by the addition of a base such as, for example, an organic tertiary nitrogen base, provided the latter is present in a limited concentration of, for example, below about 5% vol, so that the polarity of the reaction medium remains within the controlled values.

A separate solvent is not essential for the process of the invention when an excess of one of the reactants or the product will form a suitable liquid phase. From the above, it will be appreciated that the use as carrier of an excess amount of the alcohol substrate usually will not be effective. In some cases, it may be desirable to use a separate solvent. Any inert solvent can, in principle, be used for this purpose. As solvents will generally be used in fairly large amounts, it is preferred that a solvent of limited polarity is used such as solvents having an dielectric constant $\epsilon$ at 25° C. of equal or below about 6 such as, for example, an ether. Preferable solvents include aromatic hydrocarbons such as benzene ($\epsilon=2.27$), toluene ($\epsilon=2.4$) and xylenes; esters such ethyl acetate ($\epsilon=6.02$), methyl propionate ($\epsilon=5.5$) and pentenoates; and ethers such as anisole, diglyme (2,5,8-trioxanonane), diphenyl ether ($\epsilon=3.7$) and diisopropyl ether or mixtures thereof. The use of more polar aromatic N-heterocycles as solvent in amounts of higher than about 10% vol should be avoided.

Reaction conditions of temperature and pressure are the same as for previously described processes. Temperatures of from about 20 to about 200° C., more particular of from about 50 to about 150° C. are most suitable. Pressures of from about 5 to about 100, more particular of from about 25 to about 65 bar are typical. Carbon monoxide grade, reaction equipment and product purification are not critical, and well within the skills of the relevant technician.

Illustrative Embodiments

The invention will be further illustrated in detail by the following non-limiting examples.

EXAMPLE 1

A 300 ml magnetically stirred stainless steel autoclave was charged with 30 ml tert-butanol (0.32 mol), 40 ml diphenyl ether, 0.5 mmol palladium acetate, 3 mmol 1,4-di(diphenylphosphino)butane, and 10 mmol 2,4,6-trimethylbenzoic acid. The autoclave was flushed and evacuated, whereupon 20 ml of 1,3-butadiene was added and carbon monoxide was introduced to an initial carbon monoxide pressure of 30 bar. For this reaction mixture, $\epsilon_{calc}$ is 5.9. The autoclave was heated to 140° C. and the rate of pressure decrease due to carbon monoxide consumption was recorded. An initial reaction rate over the first hour of reaction of 550 mol of converted butadiene per gram atom of palladium per hour was observed. After a total reaction time of 5 hours, the autoclave was cooled and its contents analyzed by means of gas liquid chromatography (GLC). 1,3-Butadiene was found to be converted to t-butyl pentenoates with a selectivity of 95%, of which about 90% was the 3-isomers.

COMPARATIVE EXAMPLE

Example 4 of EP-A-273489 was repeated by charging an autoclave with 15 ml ethanol, 40 ml diphenyl ether, 8 ml 1,3-butadiene, 1 mmol palladium acetate, 4 mmol 1,4-di(diphenylphosphino) butane and 7.5 mmol 2,4,6-trimethylbenzoic acid. The $\epsilon_{calc}$ for this reaction mixture is 8.4. The autoclave was heated at a temperature of 150° C. and an initial reaction rate of 60 mol converted butadiene per gram atom palladium per hour was recorded.

EXAMPLES 2–6

Example 1 was repeated except for using the alcohols and their amounts in ml and mole as indicated in the below Table. As catalyst a system was used containing A: 0.5 mmol palladium acetate, 1.5 mmol 1,4-di(diphenylphosphino)butane, and 5 mmol 2,4,6-trimethylbenzoic acid; B: 0.5 mmol palladium acetate, 3 mmol 1,4-di(diphenylphosphino)butane, and 10 mmol 2,4,6-trimethylbenzoic acid, or C: 0.5 mmol palladium acetate, 3 mmol 1,4-di(diphenylphosphino)butane, and 10 mmol 2,4,6-trimethylbenzoic acid, as indicated. The Table further mentions $\epsilon_{calc}$ and the observed initial reaction rate for each Example. Selectivities to the respective alkyl pentenoates and 3-isomer contents were essentially the same as in Example 1. It is seen that high reaction rates are obtained when $\epsilon_{calc}$ is in the range according to the invention. Examples 7 and 8 are outside the scope of the invention, but show that some increase of reaction rate relative to Comparative Example can be obtained by increasing the concentration of the butadiene substrate. They also show that the much larger improvement achieved by the invention cannot satisfactorily be explained by an increase of butadiene activity in the reaction.

TABLE

| Example No. mole/gat/h | Alcohol | amount ml | amount mole | catalyst type | $\epsilon_{calc}$ | rate |
| --- | --- | --- | --- | --- | --- | --- |
| 2 | t-butanol | 30 | 0.32 | B | 5.9 | 470 |
| 3 | methanol | 5 | 0.12 | C | 5.4 | 390 |
| 4 | s-butanol | 30 | 0.33 | A | 7.3 | 275 |
| 5 | t-butanol | 15 | 0.16 | C | 4.8 | 240 |
| 6 | n-butanol | 30 | 0.33 | B | 7.8 | 200 |
| 7 | ethanol | 20 | 0.34 | A | 8.4 | 190 |
| 8 | methanol | 20 | 0.49 | B | 10.4 | 100 |

EXAMPLE 9

Example 1 was essentially repeated except for charging 20 ml tert-butanol and 10 ml methanol instead of 30 ml of tert-butanol. For this reaction mixture, $\epsilon_{calc}$ is 8.2. An initial reaction rate of 160 mole/gram atom/hour, a selectivity to methyl pentenoates of 95%, and a 3-isomer proportion of 90% were observed. This Example is for illustrative purposes and not according to the invention.

EXAMPLE 10

Example 9 was repeated except for using a mixture 25 ml tert-butanol and 5 ml methanol as the hydroxyl group-containing compound. For this reaction mixture, $\epsilon_{calc}$ is 7.1. An initial reaction rate of 315 mole/gram atom/hour was observed, the initial selectivity and 3-isomer content being the same as in Example 9.

It is seen from Examples 9 and 10, that the methyl rather than the tert-butyl esters are preferentially formed. Therefore, it is concluded that any imaginable higher reactivity of higher alcohols such as tert-butanol or isopropanol relative to lower alcohols such as ethanol or methanol would not provide a satisfactory explanation for the higher reaction rates observed in Examples 1 to 6 in accordance with the invention.

EXAMPLE 11

A 300 ml magnetically stirred stainless steel autoclave was charged with 30 ml tert-butanol (0.32 mol), 40 ml diphenyl ether, 0.5 mmol palladium acetate, 3 mmol 1,4-di(diphenylphosphino)butane, and 15 mmol 2,4,6-trimethylbenzoic acid. Furthermore, 1.2 ml of 3,4-lutidine (10 mmol) were added to the reaction mixture. The autoclave was flushed and evacuated, whereupon 20 ml of 1,3-butadiene was added and carbon monoxide was introduced to an initial carbon monoxide pressure of 30 bar. The autoclave was heated to 140° C. and the rate of pressure decrease due to carbon monoxide consumption was recorded. An initial reaction rate over the first hour of reaction of 550 mol of converted butadiene per gram atom of palladium per hour was observed. After a total reaction time of 1.5 hours, the autoclave was cooled and its contents analyzed by means of gas liquid chromatography (GLC). 1,3-Butadiene was found to be converted to t-butyl pentenoates with a selectivity of 95%, of which 92% was the 3-isomers.

It is seen that the addition of small amounts of N-heterocyclic bases does not affect the selectivity of the present process. In fact, a slight improvement of the reaction rate is observed. Since these small amounts of N-heterocyclic base are about equimolar to the acid component of the catalyst system, this embodiment of the invention allows for conducting the carbonylation process under non-acidic conditions.

EXAMPLE 12

Example 11 was essentially repeated except for adding 2.5 ml of 2,6-di-tert-butylpyridine (10 mmol) instead of 1.2 ml of 3,4-lutidine. An initial reaction rate of 550 mmol/gram atom/hour was observed.

EXAMPLE 13

A 250 ml magnetically stirred stainless steel autoclave was charged with 30 ml tert-butanol (0.32 mol), 40 ml diphenyl ether, 0.5 mmol palladium acetate, 3 mmol 1,4-di(diphenylphosphino)butane, and 15 mmol 2,4,6-trimethylbenzoic acid. Furthermore, 0.6 ml of 3,4-lutidine (5 mmol) were added to the reaction mixture. The autoclave was flushed and evacuated, whereupon 20 ml of a C4-mixture containing 11% mol of butanes, 47% mol of butenes and 42% mol of butadienes was added and carbon monoxide was introduced to an initial carbon monoxide pressure of 30 bar. The autoclave was heated to 140° C. for 5 hours, whereupon the autoclave was cooled and the pressure released. The gaseous effluent of the autoclave was analyzed and found to contain 11% mol of butadienes on the basis of total C4 content. Its liquid content was analyzed by means of GLC. The carbonylation products were found to consist for 97% mol of tert-butyl pentenoates with no pentanoates as conceivable butene carbonylation products being detected.

It is seen that butadiene can selectively be carbonylation in the presence of butenes using the present process. This is a substantial advantage as C4 mixture feedstock is readily available from cracker operations as the so-called BBB stream.

We claim:

1. A process for the preparation of alkenoic acid derivatives comprising reacting an aliphatic conjugated diene with carbon monoxide and a hydroxyl group-containing compound in a reaction medium having a calculated dielectric constant at 25° C. $\epsilon_{calc}$ of below a value of 8 in the presence of a catalyst system comprising a palladium compound, a multidentate phosphine ligand, and optionally a protonic acid.

2. The process of claim 1 wherein the calculated dielectric constant of the reaction medium is maintained at a value of $\epsilon_{calc}$ within the range of from about 4.5 to about 7.5.

3. The process of claim 2 wherein the hydroxyl group-containing compound is an alkanol having an dielectric constant $\epsilon$ at 25° C. of below 20.

4. The process of claim 3 wherein the alkanol is tert-butanol.

5. The process of claim 2 wherein the hydroxyl group-containing compound is an alkanol having an dielectric constant at 25° C. of above 20 and the concentration of said alkanol is maintained below 20% vol of the reaction medium during the course of the reaction.

6. The process of claim 5 wherein the hydroxyl group-containing compound is an alkanol having an dielectric constant at 25° C. of above 30 and the concentration of said alkanol is maintained below 12% vol of the reaction medium during the course of the reaction.

7. The process of claim 6 wherein further amounts of the alkanol are continuously or intermittently added during the course of the reaction at an rate substantially corresponding with the consumption of the alkanol.

8. The process of claim 1 wherein the reaction medium further comprise a solvent having an dielectric constant $\epsilon$ at 25° C. of equal or below about 6.

9. The process of claim 8 wherein the solvent is an ether.

10. The process of claim 1 wherein the reaction medium further comprise an organic nitrogen-containing base present at a concentration of below 5% vol.

* * * * *